US008648700B2

(12) United States Patent
Gilbert

(10) Patent No.: US 8,648,700 B2
(45) Date of Patent: Feb. 11, 2014

(54) ALERTS ISSUED UPON COMPONENT DETECTION FAILURE

(75) Inventor: Harry M. Gilbert, Portage, MI (US)

(73) Assignee: Bosch Automotive Service Solutions LLC, Warren, MI (US)

( * ) Notice: Subject to any disclaimer, the term of this patent is extended or adjusted under 35 U.S.C. 154(b) by 912 days.

(21) Appl. No.: 12/489,922

(22) Filed: Jun. 23, 2009

(65) Prior Publication Data

US 2010/0321175 A1    Dec. 23, 2010

(51) Int. Cl.
*B60Q 1/00*        (2006.01)
*G01M 17/00*     (2006.01)

(52) U.S. Cl.
USPC ... 340/425.5; 340/438; 340/439; 340/539.24; 701/29.1; 701/31.4; 701/31.5

(58) Field of Classification Search
USPC .......... 340/425.5, 438, 439, 539.24; 701/29.1
See application file for complete search history.

(56) References Cited

U.S. PATENT DOCUMENTS

| | | | |
|---|---|---|---|
| 4,404,639 A | 9/1983 | McGuire et al. | |
| 4,757,463 A | 7/1988 | Ballou et al. | |
| 4,796,206 A | 1/1989 | Boscove et al. | |
| 4,817,092 A | 3/1989 | Denny | |
| 4,866,635 A | 9/1989 | Kahn et al. | |
| 4,873,687 A | 10/1989 | Breu | |
| 4,881,230 A | 11/1989 | Clark et al. | |
| 4,943,919 A | 7/1990 | Aslin et al. | |
| 4,954,964 A | 9/1990 | Singh | |
| 4,964,125 A | 10/1990 | Kim | |
| 4,985,857 A | 1/1991 | Bajpai et al. | |
| 5,010,487 A | 4/1991 | Stonehocker | |
| 5,023,791 A | 6/1991 | Herzberg et al. | |
| 5,025,392 A | 6/1991 | Singh | |
| 5,036,479 A | 7/1991 | Prednis et al. | |
| 5,099,436 A | 3/1992 | McCown et al. | |
| 5,109,380 A | 4/1992 | Ogino | |
| 5,111,402 A | 5/1992 | Brooks et al. | |
| 5,127,005 A | 6/1992 | Oda et al. | |

(Continued)

FOREIGN PATENT DOCUMENTS

CN      1527934 A      9/2004
DE      10233503 A1    2/2004

(Continued)

OTHER PUBLICATIONS

European Search Report for Appl. No. 07252442.4, dated Sep. 11, 2007.

(Continued)

*Primary Examiner* — Donnie Crosland
(74) *Attorney, Agent, or Firm* — Baker & Hostetler LLP

(57) ABSTRACT

A system and method for alerting interested parties of component failure are provided. The system made up of a diagnostic tool for identifying a failed component, a reporting device for creating alerts, a routing device to ensure interested parties receive the proper alerts, and a memory to store information for associating parties with the alerts. Information is gathered to create an alert used to notify interested parties of instances of component failures. The alerts are routed to parties known to have an interest in the failure of the component. The system and method may provide information that allows for better planning and design of parts, greater availability to ensure a sufficient inventory of parts, more accurate diagnosis of issues, and more effective preventative maintenance.

22 Claims, 4 Drawing Sheets

(56) References Cited

U.S. PATENT DOCUMENTS

| | | |
|---|---|---|
| 5,161,158 A | 11/1992 | Chakravarty et al. |
| 5,184,312 A | 2/1993 | Ellis |
| 5,214,577 A | 5/1993 | Sztipanovits et al. |
| 5,270,920 A | 12/1993 | Pearse et al. |
| 5,293,323 A | 3/1994 | Doskocil et al. |
| 5,396,422 A | 3/1995 | Forchert et al. |
| 5,442,549 A | 8/1995 | Larson |
| 5,491,631 A | 2/1996 | Shirane et al. |
| 5,524,078 A | 6/1996 | Kolb et al. |
| 5,541,840 A | 7/1996 | Gurne et al. |
| 5,561,762 A | 10/1996 | Smith et al. |
| 5,572,424 A | 11/1996 | Kellogg et al. |
| 5,586,252 A | 12/1996 | Barnard et al. |
| 5,617,039 A | 4/1997 | Kuck et al. |
| 5,631,831 A | 5/1997 | Bird et al. |
| 5,670,939 A | 9/1997 | Rodewald et al. |
| 5,671,141 A | 9/1997 | Smith et al. |
| 5,696,676 A | 12/1997 | Takaba |
| 5,729,452 A | 3/1998 | Smith et al. |
| 5,742,500 A | 4/1998 | Irvin |
| 5,778,381 A | 7/1998 | Sandifer |
| 5,835,871 A | 11/1998 | Smith et al. |
| 5,838,261 A | 11/1998 | Lauta et al. |
| 5,852,789 A | 12/1998 | Trsar et al. |
| 5,883,586 A | 3/1999 | Tran et al. |
| 5,916,286 A | 6/1999 | Seashore et al. |
| 5,964,811 A | 10/1999 | Ishii et al. |
| 5,964,813 A | 10/1999 | Ishii et al. |
| 5,987,443 A | 11/1999 | Nichols et al. |
| 6,003,021 A | 12/1999 | Zadik et al. |
| 6,003,808 A | 12/1999 | Nguyen et al. |
| 6,006,146 A | 12/1999 | Usui et al. |
| 6,012,152 A | 1/2000 | Douik et al. |
| 6,032,088 A | 2/2000 | Feldmann et al. |
| 6,041,287 A | 3/2000 | Dister et al. |
| 6,055,468 A | 4/2000 | Kaman et al. |
| 6,064,998 A | 5/2000 | Zabloudil et al. |
| 6,067,537 A | 5/2000 | O'Connor et al. |
| 6,067,538 A | 5/2000 | Zorba et al. |
| 6,073,127 A | 6/2000 | Lannert et al. |
| 6,085,184 A | 7/2000 | Bertrand et al. |
| 6,119,074 A | 9/2000 | Sarangapani |
| 6,122,575 A | 9/2000 | Schmidt et al. |
| 6,134,488 A | 10/2000 | Sasaki et al. |
| 6,141,608 A | 10/2000 | Rother |
| 6,167,352 A | 12/2000 | Kanevsky et al. |
| 6,175,787 B1 | 1/2001 | Breed |
| 6,192,302 B1 | 2/2001 | Giles et al. |
| 6,205,465 B1 | 3/2001 | Schoening et al. |
| 6,226,627 B1 | 5/2001 | Polak |
| 6,236,917 B1 | 5/2001 | Liebl et al. |
| 6,249,755 B1 | 6/2001 | Yemini et al. |
| 6,263,268 B1 * | 7/2001 | Nathanson ............ 701/31.5 |
| 6,263,322 B1 | 7/2001 | Kirkevold et al. |
| 6,282,469 B1 | 8/2001 | Rogers et al. |
| 6,301,531 B1 | 10/2001 | Pierro et al. |
| 6,314,375 B1 | 11/2001 | Sasaki et al. |
| 6,330,499 B1 * | 12/2001 | Chou et al. ............ 701/31.4 |
| 6,338,148 B1 | 1/2002 | Gillenwater et al. |
| 6,363,304 B1 | 3/2002 | Ramsey |
| 6,434,455 B1 * | 8/2002 | Snow et al. ............ 701/31.4 |
| 6,477,453 B2 | 11/2002 | Oi et al. |
| 6,493,615 B1 | 12/2002 | Johnston |
| 6,505,106 B1 | 1/2003 | Lawrence et al. |
| 6,512,968 B1 | 1/2003 | de Bellefeuille et al. |
| 6,522,987 B1 | 2/2003 | Flink et al. |
| 6,526,340 B1 | 2/2003 | Reul et al. |
| 6,526,361 B1 | 2/2003 | Jones et al. |
| 6,538,472 B1 | 3/2003 | McGee |
| 6,557,115 B2 | 4/2003 | Gillenwater et al. |
| 6,560,516 B1 | 5/2003 | Baird et al. |
| 6,574,537 B2 | 6/2003 | Kipersztok et al. |
| 6,591,182 B1 | 7/2003 | Cece et al. |
| 6,609,051 B2 | 8/2003 | Fiechter et al. |
| 6,611,740 B2 | 8/2003 | Lowrey et al. |
| 6,615,120 B1 | 9/2003 | Rother |
| 6,636,790 B1 | 10/2003 | Lightner et al. |
| 6,640,166 B2 | 10/2003 | Liebl et al. |
| 6,643,607 B1 | 11/2003 | Chamberlain et al. |
| 6,652,169 B2 | 11/2003 | Parry |
| 6,662,087 B1 | 12/2003 | Liebl et al. |
| 6,694,235 B2 | 2/2004 | Akiyama |
| 6,708,092 B1 | 3/2004 | Starks et al. |
| 6,711,134 B1 | 3/2004 | Wichelman et al. |
| 6,714,846 B2 | 3/2004 | Trsar et al. |
| 6,738,697 B2 | 5/2004 | Breed |
| 6,748,304 B2 | 6/2004 | Felke et al. |
| 6,751,536 B1 | 6/2004 | Kipersztok et al. |
| 6,768,935 B1 | 7/2004 | Morgan et al. |
| 6,795,778 B2 | 9/2004 | Dodge et al. |
| 6,807,469 B2 | 10/2004 | Funkhouser et al. |
| 6,819,988 B2 | 11/2004 | Dietz et al. |
| 6,836,708 B2 | 12/2004 | Tripathi |
| 6,845,307 B2 | 1/2005 | Rother |
| 6,845,468 B2 | 1/2005 | James |
| 6,868,319 B2 | 3/2005 | Kipersztok et al. |
| 6,874,680 B1 | 4/2005 | Klaus et al. |
| 6,928,349 B1 | 8/2005 | Namaky et al. |
| 6,941,203 B2 * | 9/2005 | Chen ............ 701/31.6 |
| 6,950,829 B2 | 9/2005 | Schlabach et al. |
| 6,993,421 B2 | 1/2006 | Pillar et al. |
| 7,010,460 B2 | 3/2006 | Trsar et al. |
| 7,013,411 B2 | 3/2006 | Kallela et al. |
| 7,050,894 B2 | 5/2006 | Halm et al. |
| 7,062,622 B2 | 6/2006 | Peinado |
| 7,073,120 B2 | 7/2006 | Torii et al. |
| 7,082,359 B2 | 7/2006 | Breed |
| 7,103,610 B2 | 9/2006 | Johnson et al. |
| 7,103,679 B2 | 9/2006 | Bonn |
| 7,120,559 B1 | 10/2006 | Williams et al. |
| 7,120,890 B2 | 10/2006 | Urata et al. |
| 7,124,058 B2 | 10/2006 | Namaky et al. |
| 7,142,960 B2 | 11/2006 | Grier et al. |
| 7,162,741 B2 | 1/2007 | Eskin et al. |
| 7,165,216 B2 | 1/2007 | Chidlovskii et al. |
| 7,171,372 B2 | 1/2007 | Daniel et al. |
| 7,203,881 B1 | 4/2007 | Williams et al. |
| 7,209,815 B2 | 4/2007 | Grier et al. |
| 7,209,817 B2 | 4/2007 | Abdel-Malek et al. |
| 7,209,860 B2 | 4/2007 | Trsar et al. |
| 7,216,052 B2 | 5/2007 | Fountain et al. |
| 7,251,535 B2 | 7/2007 | Farchmin et al. |
| 7,272,475 B2 | 9/2007 | Gawlik et al. |
| 7,272,756 B2 | 9/2007 | Brink et al. |
| 7,286,047 B2 | 10/2007 | Oesterling et al. |
| 7,373,225 B1 | 5/2008 | Grier et al. |
| 7,376,497 B2 | 5/2008 | Chen |
| 7,379,846 B1 | 5/2008 | Williams et al. |
| 7,400,954 B2 | 7/2008 | Sumcad et al. |
| 7,409,317 B2 | 8/2008 | Cousin et al. |
| 7,428,663 B2 | 9/2008 | Morton et al. |
| 7,430,535 B2 | 9/2008 | Dougherty et al. |
| 7,444,216 B2 | 10/2008 | Rogers et al. |
| 7,483,774 B2 | 1/2009 | Grichnik et al. |
| 7,555,376 B2 | 6/2009 | Beronja |
| 7,565,333 B2 | 7/2009 | Grichnik et al. |
| 7,610,127 B2 | 10/2009 | D'Silva et al. |
| 7,636,622 B2 | 12/2009 | Underdal et al. |
| 7,643,912 B2 | 1/2010 | Heffington |
| 7,643,916 B2 | 1/2010 | Underdal et al. |
| 7,647,349 B2 | 1/2010 | Hubert et al. |
| 7,715,961 B1 | 5/2010 | Kargupta |
| 7,739,007 B2 | 6/2010 | Logsdon |
| 7,751,955 B2 | 7/2010 | Chinnadurai et al. |
| 7,752,224 B2 | 7/2010 | Davis et al. |
| 7,761,591 B2 | 7/2010 | Graham |
| 7,765,040 B2 | 7/2010 | Underdal et al. |
| 7,778,746 B2 | 8/2010 | McLeod et al. |
| 7,788,096 B2 | 8/2010 | Chelba et al. |
| 7,809,482 B2 | 10/2010 | Bertosa et al. |
| 7,853,435 B2 | 12/2010 | Dodge et al. |
| 7,860,620 B2 | 12/2010 | Kojitani et al. |
| 7,865,278 B2 | 1/2011 | Underdal et al. |
| 7,882,394 B2 | 2/2011 | Hosek et al. |

(56) References Cited

U.S. PATENT DOCUMENTS

| | | | |
|---|---|---|---|
| 7,925,397 | B2 | 4/2011 | Underdal et al. |
| 8,019,501 | B2 | 9/2011 | Breed |
| 8,024,083 | B2 * | 9/2011 | Chenn .................. 701/31.5 |
| 8,055,907 | B2 | 11/2011 | Deem et al. |
| 8,239,094 | B2 | 8/2012 | Underdal et al. |
| 2002/0007237 | A1 | 1/2002 | Phung et al. |
| 2002/0059075 | A1 | 5/2002 | Schick et al. |
| 2002/0091736 | A1 | 7/2002 | Wall |
| 2002/0112072 | A1 | 8/2002 | Jain |
| 2002/0116669 | A1 | 8/2002 | Jain |
| 2002/0173885 | A1 | 11/2002 | Lowrey et al. |
| 2003/0177414 | A1 | 9/2003 | Pillutla et al. |
| 2004/0001106 | A1 | 1/2004 | Deutscher et al. |
| 2004/0039493 | A1 | 2/2004 | Kaufman |
| 2004/0181688 | A1 | 9/2004 | Wittkotter |
| 2005/0043868 | A1 | 2/2005 | Mitcham |
| 2005/0065678 | A1 | 3/2005 | Smith et al. |
| 2005/0071143 | A1 | 3/2005 | Tran et al. |
| 2005/0137762 | A1 | 6/2005 | Rother |
| 2005/0144183 | A1 | 6/2005 | McQuown et al. |
| 2005/0177352 | A1 | 8/2005 | Gravel |
| 2005/0222718 | A1 | 10/2005 | Lazarz et al. |
| 2006/0030981 | A1 | 2/2006 | Robb et al. |
| 2006/0074824 | A1 | 4/2006 | Li |
| 2006/0095230 | A1 | 5/2006 | Grier et al. |
| 2006/0129906 | A1 | 6/2006 | Wall |
| 2006/0136104 | A1 | 6/2006 | Brozovich et al. |
| 2006/0142907 | A1 | 6/2006 | Cancilla et al. |
| 2006/0142910 | A1 | 6/2006 | Grier et al. |
| 2006/0149434 | A1 | 7/2006 | Bertosa et al. |
| 2006/0210141 | A1 | 9/2006 | Kojitani et al. |
| 2006/0229777 | A1 | 10/2006 | Hudson et al. |
| 2007/0100520 | A1 | 5/2007 | Shah et al. |
| 2007/0124282 | A1 | 5/2007 | Wittkotter |
| 2007/0226540 | A1 | 9/2007 | Konieczny |
| 2007/0250228 | A1 | 10/2007 | Reddy et al. |
| 2007/0293998 | A1 | 12/2007 | Underdal et al. |
| 2007/0294001 | A1 | 12/2007 | Underdal et al. |
| 2009/0216584 | A1 | 8/2009 | Fountain et al. |
| 2009/0271066 | A1 | 10/2009 | Underdal et al. |
| 2010/0082197 | A1 | 4/2010 | Kolbet et al. |
| 2010/0262431 | A1 | 10/2010 | Gilbert |

FOREIGN PATENT DOCUMENTS

| | | | |
|---|---|---|---|
| DE | 10332203 | A1 | 2/2005 |
| EP | 1674958 | B1 | 2/2008 |
| GB | 2329943 | A | 4/1999 |
| JP | H03-087671 | A | 4/1991 |
| JP | 06-265596 | A | 9/1994 |
| JP | H08-043265 | A | 2/1996 |
| JP | H10-253504 | A | 9/1998 |
| JP | 2001-202125 | A | 7/2001 |
| JP | 2001-229299 | A | 8/2001 |
| JP | 2002-183334 | A | 6/2002 |
| JP | 2004-299587 | A | 10/2004 |
| JP | 2007-326425 | A | 12/2007 |

OTHER PUBLICATIONS

European Search Report for Appl. No. 07252441, dated Jun. 20, 2008.

L.J. Aartman, et al., "An Independent Verification Tool for Multi-Vendor Mode S Airborne Transponder Conformance Testing," 21$^{st}$ Digital Avionics Systems Conference, 2002, pp. 12.E.5-1—12.E.5-11. vol. 2.

"Annex A Test Bit Sequence," Methodology for Jitter and Signal Quality; Specification-MJSQ Technical Report REV 10.0, pp. 117-132, Mar. 10, 2003.

Tariq Assaf, et al. "Automatic Generation of Diagnostic Expert Systems from Fault Trees," 2003 Proceedings Annual Reliability & Maintainability Symposium, pp. 143-147.

R. Belhassine-Cherif, et al., "Multiple Fault Diagnostics for Communicating Nondeterministic Finite State Machines," 6$^{th}$ IEEE Symposium on Computers and Communications, Jul. 3-5, 2001, pp. 661-666.

M. Ben-Bassat, et al., "A1-Test: A Real Life Expert System for Electronic Troubleshooting (A Description and a Case Study)," 4$^{th}$ Conference on Artificial Intelligence Applications, 1988. pp. 2-10.

F. Brajou, et al., "The Airbus A380—An AFDX-Based Flight Test Computer Concept," 2004 IEEE AUTOTESTCON, pp. 460-463.

Cantone, et al., "IN-ATE: Fault Diagnosis as Expert System Guided Search," Computer Expert Systems, L. Bolc & M.J. Coombs (eds.), Springer-Verlag, New York 1986, pp. 298348.

"Computerized Diagnostic Tester at Hand," Electrical World, Aug. 1, 1975, pp. 36-38.

T.A. Cross, "A Digital Electronic System for Automobile Testing and Diagnosis," IEE Conference Jul. 6-9, 1976, London, England, pp. 152-159.

eHow Contributor, "How to Organize Computer Files," printed Mar. 31, 2011 from http://www.ehow.com/print/how_138482_organize-computer-files.html.

F. Esposito, et al., "Machine Learning Methods for Automatically Processing Historical Documents: from Paper Acquisition to XML Transformation," 1$^{st}$ Int'l Workshop on Document Image Analysis for Libraries. Jan. 23-24. 2004, pp. 328-335.

H. Garcia-Molina, et al., "dSCAM: Finding Document Copies Across Multiple Databases," 4th Int'l Conference on Parallel and Distributed Information Systems, Dec. 18-20, 1996, pp. 68-79.

I. Ghosh, et al., "Automatic Test Pattern Generation for Functional Register-Transfer Level Circuits Using Assignment Decision Diagrams," IEEE Transactions on Computer-Aided Design of Integrated Circuits and Systems, vol. 20, Issue 3, Mar. 2001. pp. 402-415.

B. Ives et al., "After the Sale: Leveraging Maintenance with Information Technology," MIS Quarterly, vol. 12, No. 1, Mar. 1988, pp. 7-21.

M. Koppel, et al., "Automatically Classifying Documents by Ideological and Organizational Affiliation," IEEE Int'l Conference on Intelligence and Security Informatics, Jun. 8-11, 2009, pp. 176-178.

J.C. Lin, et al., "Using Genetic Algorithms for Test Case Generation in Path Testing," 9$^{th}$ Asian Test Symposium, Dec. 4-6, 2000, pp. 241-246.

W. Linzhang, et al., "Generating Test Cases from UML Activity Diagram Based on Gray-Box Method," 11$^{th}$ Asia-Pacific Software Engineering Conference, Nov. 30-Dec. 3, 2004, pp. 1-8.

B.D. Liu, et al., "Efficient Global Strategy for Designing and Testing Scanned Sequential Circuits," IEE Proceedings on Computers and Digital Techniques, vol. 142, No. 2, Mar. 1995, pp. 170-176.

M. Mayer, "The Computerized Diagnostic Rhyme Test as a Design Tool for Armored Vehicle Intercommunications Systems," Military Communications Conference, 1985, pp. 166-170.

Microsoft at Work, "File Organization tips: 9 ideas for managing files and folders," printed Mar. 30, 2011 from http://www.microsoft.com/atwork/productivity/files.aspx.

S.M. Namburu, et al., "Systematic Data-Driven Approach to Real-Time Fault Detection and Diagnosis in Automotive Engines," 2006 IEEE AUTOTESTCON, pp. 59-65.

"Names files and folders—How to—Web Team—University of Canterbury, New Zealand," printed on Mar. 31, 2011 from http://www.canterbury.ac.nz/web/how/filename.shtml.

D. Niggemeyer, et al., "Automatic Generation of Diagnostic Mar. Tests," 19$^{th}$ IEEE Proceedings on VLSI Test Symposium, 2001, pp. 299-304.

Yiannis Papadopoulos, et al., "Automating the Failure Modes and Effects Analysis of Safety Critical Systems," Proceedings of the Eighth IEEE Int'l Symposium on High Assurance Systems Engineering (HASE '04), 2004.

F.C. Pembe, et al., "Heading-Based Sectional Hierarchy Identification for HTML Documents," 22$^{nd}$ Int'l Symposium on Computer and Information Sciences, Nov. 7-9, 2007, pp. 1-6.

F. Pipitone, "The FIS Electronics Troubleshooting System Guided Search," Computer Expert Systems, vol. 19, No. 7, 1986, pp. 68-76.

G. Qin, et al., "On-Board Fault Diagnosis of Automated Manual Transmission Control System," IEEE Transactions on Control Systems Technology, vol. 12, No. 4, Jul. 2004, pp. 564-568.

(56) References Cited

OTHER PUBLICATIONS

H.M.T. Saarikoski, "2T: Two-Term Indexing of Documents Using Syntactic and Semantic Constraints," 16$^{th}$ Int'l Workshop on Database and Expert Systems Applications, Aug. 22-26, 2005, pp. 1025-1028.

P. Samuel, et al., "UML Sequencing Diagram Based Testing Using Slicing," An Int'l Conference of IEEE India Council, Dec. 11-13, 2005, pp. 176-178.

F.Y. Shih, et al., "A Document Segmentation, Classification and Recognition System," 2$^{nd}$ Int'l Conference on Systems Integration, 1992, pp. 258-267.

H. Trier, "Further Development of the Periodical Vehicle Test by Using Diagnostic Interface," IEE Colloquium on Vehicle Diagnostics in Europe, 1994, pp. 4/1-4/2.

J. van Beers, et al., "Test Features of a Core-Based Co-Processor Array for Video Applications," Int'l Test Conference, 1999, pp. 638-647.

"Volkswagon-Audi Vehicle Communication Software Manual," Snap-On, published Mar. 31, 2006, http://www.w124performance.com/docs/general/Snap-On/manuals/VCS_Manual_VW_Audi.pdf, XP007920392.

J.R. Wagner, "Failure Mode Testing Tool Set for Automotive Electronic Controllers," IEEE Transactions on Vehicular Technology, vol. 43, Issue 1, Feb. 1994, pp. 156-163.

Reuben Wright, et al., "How Can Ontologies Help Repair Your Car?" XTECH 2005: XML, the Web and beyond; May 27, 2005, Amsterdam; http://ww.idealliance.org/proceedings/xtech05/papers/02-07-02/.

* cited by examiner

ALERTS ISSUED UPON COMPONENT DETECTION FAILURE

FIELD OF THE INVENTION

The present invention relates generally to diagnostic equipment. More particularly, the present invention relates to implementation of alerts issued within a system upon the identification of a failed component through a diagnostic procedure for different types of diagnosed items, for example, a vehicle.

BACKGROUND OF THE INVENTION

In many industries, diagnostic systems play an increasingly important role in manufacturing processes, as well as in maintenance and repair throughout the lifetime of the equipment or product. Some diagnostic systems are based on personal computer technology and feature user-friendly, menu-driven diagnostic applications. These systems assist technicians and professionals at all levels in performing system diagnostics on a real-time basis.

A typical diagnostic system includes a display on which instructions for diagnostic procedures are displayed. The system also includes a system interface that allows the operator to view real-time operational feedback and diagnostic information. Thus, the operator may view, for example, vehicle engine speed in revolutions per minute, or battery voltage during start cranking; or a patient's heartbeat rate or blood pressure. With such a system, a relatively inexperienced operator may perform advanced diagnostic procedures and diagnose complex operational or medical problems.

It is desirable to provide a method and apparatus to identify all of the known failures associated with a vehicle component, and for informing interested parties of instances of those failures associated with the component. Further, identification of failed components may lead to identification of a specific problem and can lead to greater accuracy and efficiency in fixing or even avoiding the problem with the component.

SUMMARY OF THE INVENTION

The foregoing needs are met, to a great extent, by the present invention, wherein in one aspect, a method and system are provided such that in some embodiments alerts of a component failure are sent to interested parties.

In accordance with one embodiment of the present invention, a method for notifying an interested party of a component failure can involve identifying a failed vehicle component through vehicle diagnostics, creating an alert, in a reporting device, by incorporating an identity information and a failure information for the failed vehicle component, transferring the alert to a routing device, and sending the alert from the routing device via electronic communication to the interested party.

In accordance with yet another embodiment of the present invention, a system for notifying an interested party is provided which can include a portable vehicle diagnostic tool to identify a failed vehicle component and a related failure for the failed vehicle component, a reporting device communicatively connected to the portable vehicle diagnostic tool, to create an alert containing information about the failed vehicle component and the failure identified by the portable vehicle diagnostic tool and to send the alert, a routing device communicatively connected to the reporting device to route the alert to the interested party, a memory communicatively connected to the routing device to store information relating the interested party with information that may exist in the alert, and a communication network communicatively connecting the portable vehicle diagnostic tool, the reporting device, and the routing device.

In accordance with still another embodiment of the present invention, a system for notifying an interested party is provided, which can include a means for identifying a failed vehicle component, a means for creating an alert by incorporating identity information and failure information for the failed vehicle component, a means for sending the alert via electronic communication to the interested party, a means for transferring the alert to the means for sending, and a means for communicatively connecting the other means.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
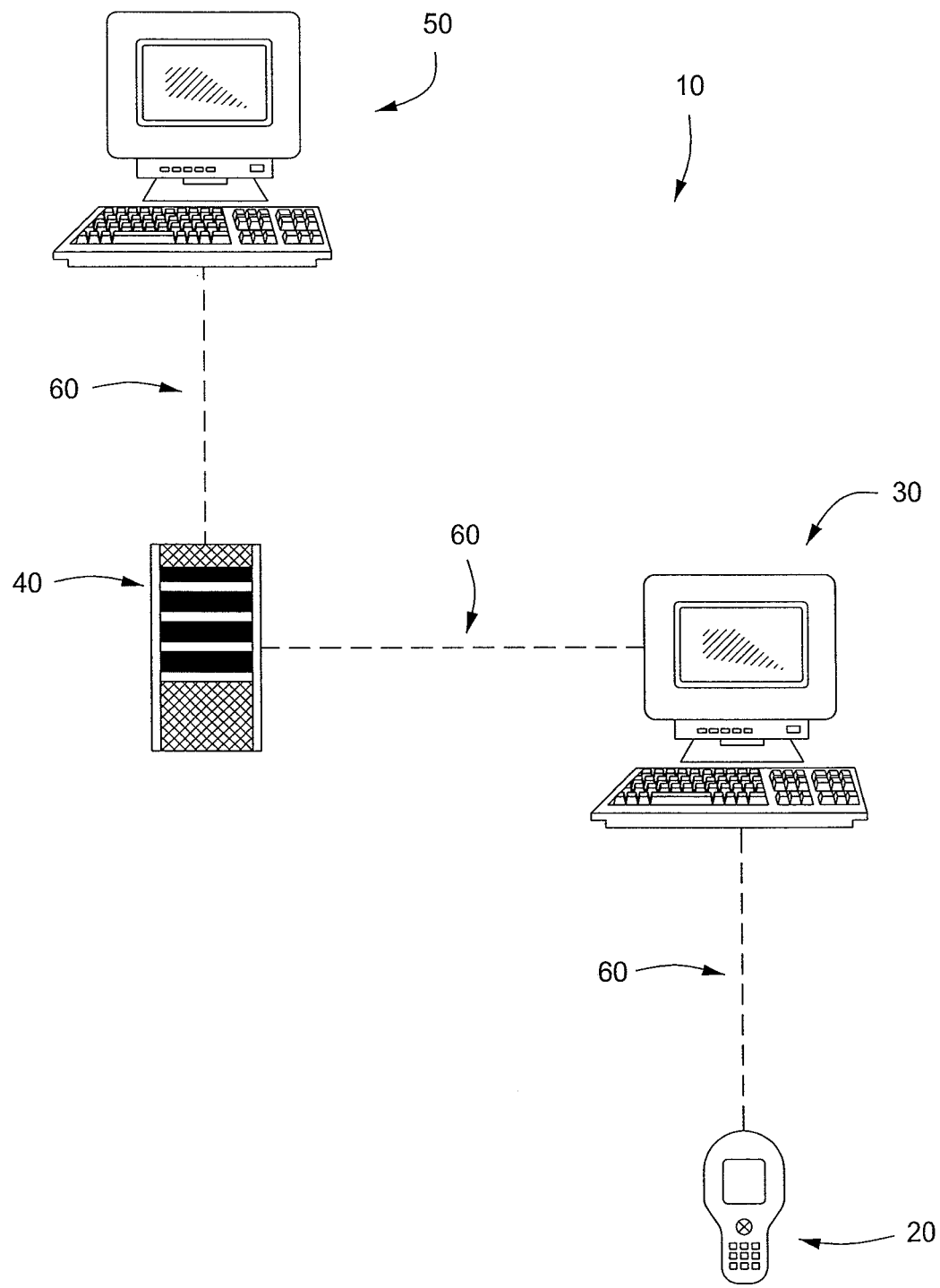
FIG. 1 is a schematic diagram illustrating a system for notifying interested parties upon component failure according to an embodiment of the invention.

An embodiment of the present inventive method and system for notifying interested parties can provide a portable vehicle diagnostic tool to identify a failed vehicle component. The portable vehicle diagnostic tool can perform a combination of functions. Such functions may include diagnostic testing on vehicle components and systems, data analysis, and provide historical data. A portable vehicle diagnostic tool may use its functionality to help a technician determine if there is a vehicle component failure and if so, which component has failed. In other embodiments, the portable vehicle diagnostic tool can itself determine if there is a vehicle component failure and if so, which component has failed. Further, it may be possible for the portable vehicle diagnostic tool to help, or itself, determine the particular failure for the failed vehicle component. Such a failure may be indicated by a failure code or a written description of the failure.

In addition to the portable vehicle diagnostic tool, the method and system may provide a reporting device connected to or as a part of the portable vehicle diagnostic tool. The reporting device creates the alerts by bundling the desired information into a format that can be sent to, received by, and understood by the interested parties. The information may be bundled into a number of different file formats, for example a text file or an XML file. The information included in the alerts created by the reporting device may include what is the failed vehicle component. Other information that could be useful to the interested parties may be included as well, such as diagnostic data or vehicle data associated with the component.

The method and system may further provide a routing device, which may be another component of any of the previous devices or device combinations, or may be a separate device. The routing device may serve to ensure that that the interested parties are sent the proper alerts. That is, the routing device may be able to match the information in the alerts to other information that details what alerts different parties would be interested in receiving. The parties may include the component manufacturer, an auto parts store, a fleet maintenance manager and other parties that are interested in what components fail in a vehicle. Once determining which parties are to receive the alerts, the routing device may push the alerts to the recipients.

Another component of the method and system may be a memory to store information for associating parties with the alerts. The information stored in this memory may be used by the routing device so that it may perform its functions. The memory may store its information in a database or may employ other data structures to relate the information in memory together. Like the routing device, the memory may be a device on its own, or it may be a device in combination with any or all of the previous devices or device combinations.

Alternatively, the routing device and memory may serve to verify requests for information instead of determining where to send the information based on its own determinations. This may occur in a method and system employing a pull protocol, such as Really Simple Syndication (RSS). The routing device could receive requests for information, and if such information exists, check the memory for information allowing the requesting devices access to the desired information. If the request is valid, then the routing device may send the alert to the interested parties.

Optionally, the method and system may provide for a receiving device. This receiving device could remain idle in terms of its interaction with the method and system until a component fails, and an alert is created and the routing device determines the receiving device belongs to an interested party and sends the alert. At that point the receiving device will receive the alert. Alternatively, the receiving device may make requests to the routing device for information.

The invention will now be described with reference to the drawing figures, in which like reference numerals refer to like parts throughout. An embodiment of the present inventive system is illustrated in FIG. 1, which illustrates a system for notifying interested parties upon component failure 10 (component failure notification system) according to an embodiment of the invention. The component failure notification system 10 can gather information about the failure of a component and send an alert of the failure to interested parties. The alerts, or notifications, provide pertinent information about component failures to those parties who are interested in knowing that a certain component has failed. Through application of the component failure notification system 10, the parties receiving the information on the failed components can make reactionary decisions to the information, such as to avoid potential problems related to the component failure, to produce more of the component or have more of the component in inventory, or to improve on the component such that the failure occurs less often. These reactionary measures are implemented after the receipt and analysis of the information provided by the component failure notification system 10.

The component failure notification system 10 can include a portable vehicle diagnostic tool 20, a reporting device 30, a routing device 40, and an optional receiving device 50. Each of the portable vehicle diagnostic tool 20, the reporting device 30, the routing device 40, and the receiving device 50 can include an input device, a memory, a communication device, a processor, and a display, all of which can be interconnected by a data link. The portable vehicle diagnostic tool 20, the reporting device 30, the routing device 40, and the receiving device 50 can be a general computing device, such as a personal computer (PC), a UNIX workstation, a server, a mainframe computer, a personal digital assistant (PDA), smartphone, cellular phone, or some combination of these. Alternatively, the portable vehicle diagnostic tool 20, the reporting device 30, the routing device 40, and the receiving device 50 can be a specialized computing device, such as a vehicle diagnostic scan tool. The remaining components can include programming code, such as source code, object code or executable code, stored on a computer-readable medium that can be loaded into the memory and processed by the processor in order to perform the desired functions of the component failure notification system 10.

In various embodiments, the portable vehicle diagnostic tool 20, the reporting device 30, the routing device 40, and the receiving device 50 can be coupled to a communication network 60, which can include any viable combination of devices and systems capable of linking computer-based systems, such as the Internet; an intranet or extranet; a local area network (LAN); a wide area network (WAN); a direct cable connection; a private network; a public network; an Ethernet-based system; a token ring; a value-added network; a telephony-based system, including, for example, T1 or E1 devices; an Asynchronous Transfer Mode (ATM) network; a wired system; a wireless system; an optical system; cellular system; satellite system; a combination of any number of distributed processing networks or systems or the like. The communication network 60 allows for communication between the portable vehicle diagnostic tool 20, the reporting device 30, the routing device 40, and the receiving device 50.

The portable vehicle diagnostic tool 20, the reporting device 30, the routing device 40, and the receiving device 50 can be coupled to the communication network 60 by way of the communication device, which in various embodiments can incorporate any combination of devices—as well as any associated software or firmware-configured to couple processor-based systems, such as modems, network interface cards, serial buses, parallel buses, LAN or WAN interfaces, wireless or optical interfaces and the like, along with any associated transmission protocols, as may be desired or required by the design.

Additionally, an embodiment of the component failure notification system 10 can communicate information to the user through the display and request user input through the input device, by way of an interactive, menu-driven, visual display-based user interface, or graphical user interface (GUI). Alternatively, the communication can be text based only, or a combination of text and graphics. The user interface can be executed, for example, on a personal computer (PC) with a mouse and keyboard, with which the user may interactively input information using direct manipulation of the GUI. Direct manipulation can include the use of a pointing device, such as a mouse or a stylus, to select from a variety of selectable fields, including selectable menus, drop-down menus, tabs, buttons, bullets, checkboxes, text boxes, and the like. Nevertheless, various embodiments of the invention may incorporate any number of additional functional user interface schemes in place of this interface scheme, with or without the use of a mouse or buttons or keys, including for example, a trackball, a scroll wheel, a touch screen or a voice-activated system.

Some applications of the component failure notification system 10 may not require that all of the elements of the system be separate pieces. Having the portable vehicle diagnostic tool 20, the reporting device 30 and the routing device 40 as separate devices within the component failure notification system 10 provides certain flexibilities. For example, in a nationwide implementation, the routing device 40 may be a centralized device hosted by an entity in a remote location. Then individual service shops, for example, may each have a reporting device 30 that forwards alerts to the routing device 40 to disseminate the alerts to the interested individuals. Further, large service shops may have multiple portable vehicle diagnostic tools 20 to provide information to the reporting device. However, this type of implementation may have greater costs associated with it because of all the separate pieces. Therefore, the component failure notification system 10 encompasses multiple embodiments.

Figure 2:
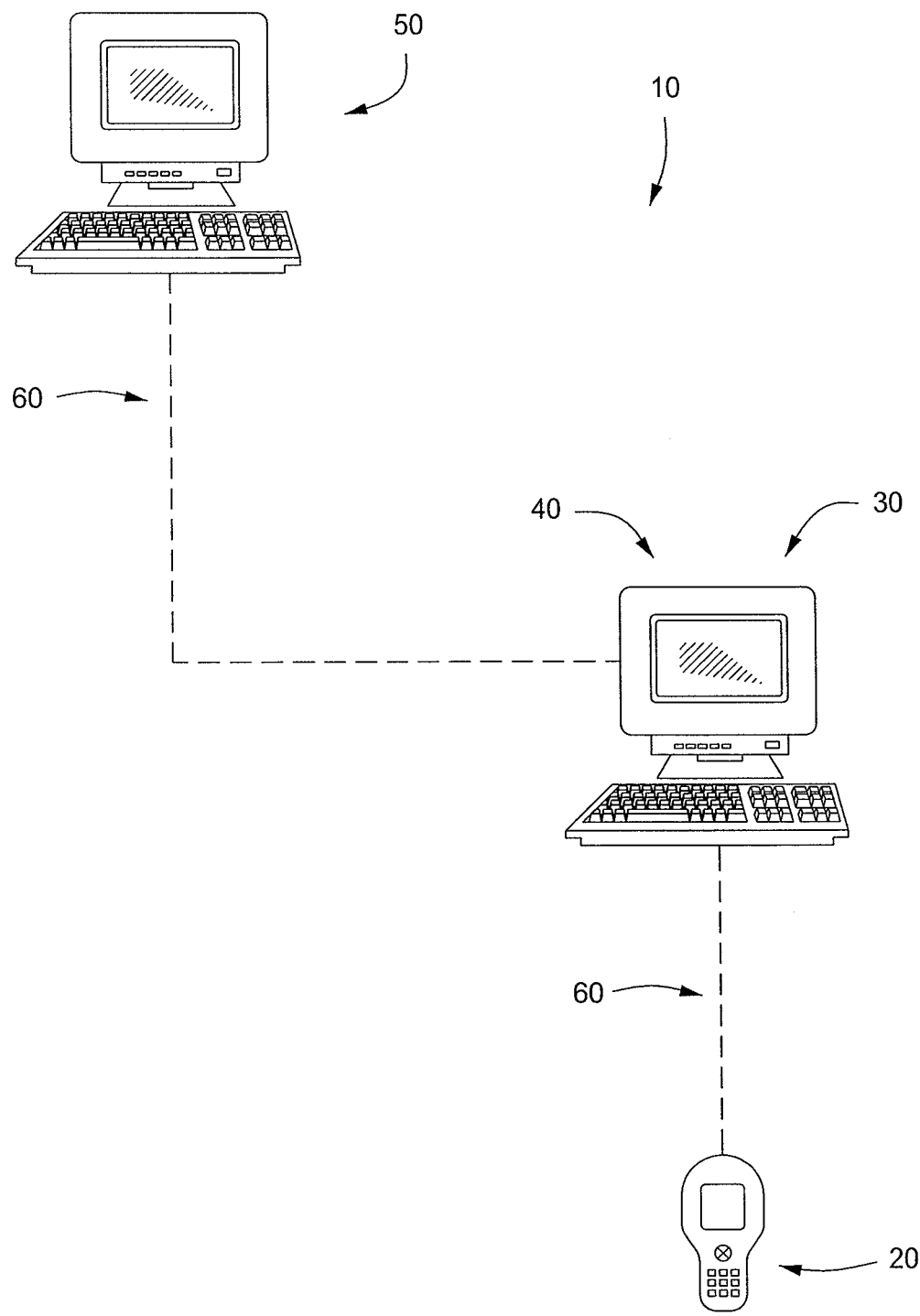
FIG. 2 is a schematic diagram illustrating a system for notifying interested parties upon component failure according to another embodiment of the invention.

Referring now to FIG. 2, which illustrates the component failure notification system 10 according to an embodiment of the invention, the reporting device 30 and the routing device 40 make up a singular unit. In this embodiment, two portions of the component failure notification system 10 which were previously described as separate are now, alternatively, one physical element. Such an embodiment could be useful in implementing the component failure notification system 10 within a single company having a large service or testing facility. Such an environment may require the use of multiple portable vehicle diagnostic tools 20, but since all of the information is gathered in a relatively small number of locations where it is relatively simple to connect all of the portable vehicle diagnostic tools to one reporting device 30, there is no need for a routing device 40 to reside separately.

Figure 3:
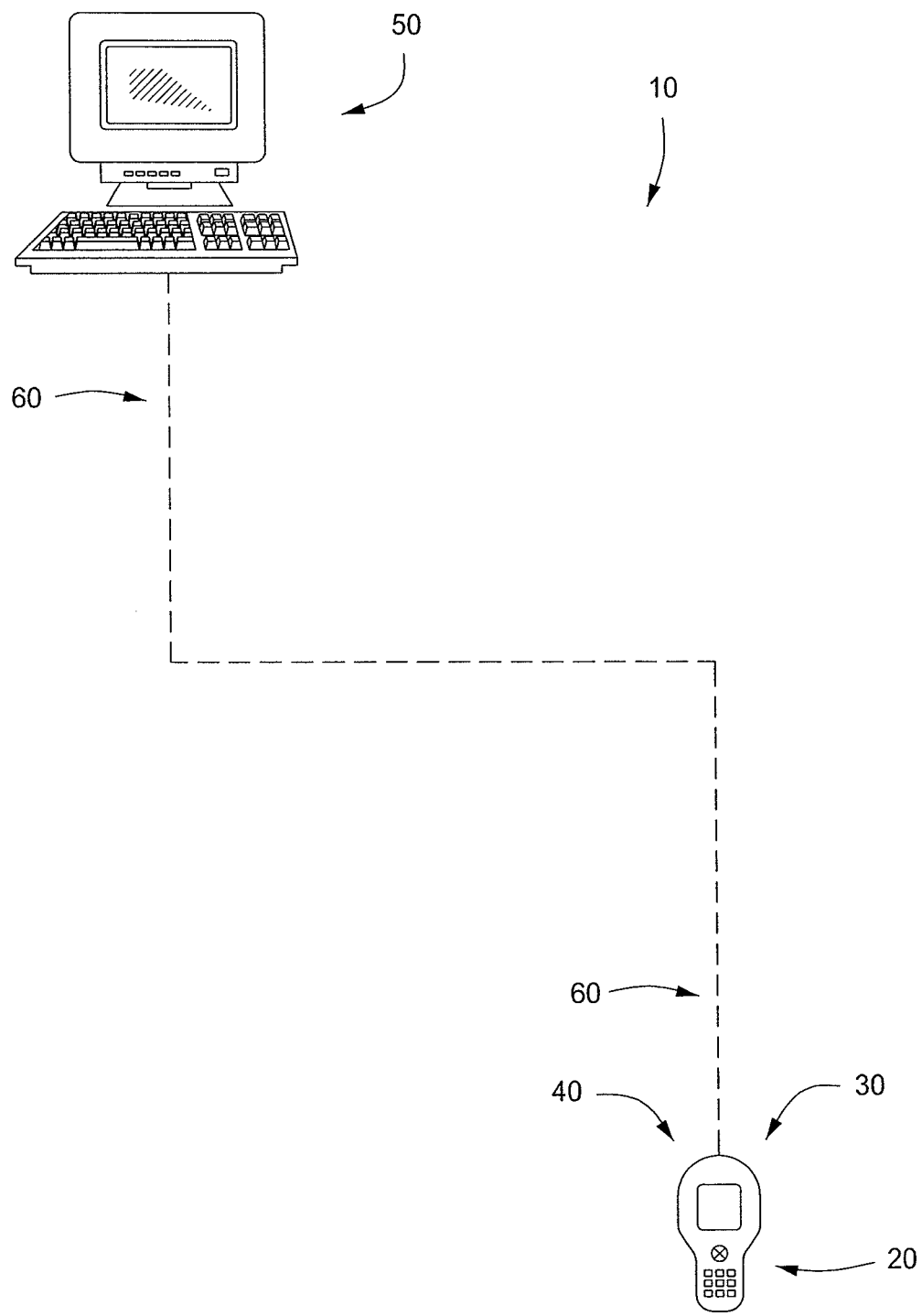
FIG. 3 is a schematic diagram illustrating a system for notifying interested parties upon component failure according to still another embodiment of the invention.

Another alternative embodiment is depicted in the FIG. 3. For even smaller operations than the ones already described, it may be that integrating the portable vehicle diagnostic tool 20, the reporting device 30, and the routing device 40 into a single unit is the most cost effective choice. In the instance where a user, may be a small company with limited need for testing and diagnostic equipment, and reports its component failure information to a select group, it may not be necessary to implement a system to capture multiple sources of information in a centralized location to properly determine how to disseminate it. Therefore, a small number of devices, including the portable vehicle diagnostic tool 20, the reporting device 30, and the routing device 40, may be sufficient to gather, package, and route the information to the desired recipients without incurring unnecessary expense.

A memory may exist in all of the embodiments of the component failure notification system 10. It may exist separately or as a component of any of the portable vehicle diagnostic tool 20, the reporting device 30, and the routing device 40, or any combination thereof. This memory may contain information such that the routing device 40 may determine which alerts are pertinent to which of the parties. Such information would allow the routing device 40 to compare the information from the alert to the preferences of any of the parties to determine if the alert is of interest to the parties. Once the determination is made that the alert should be sent to the parties, then the routing device 40 may send the alert.

An alternative, but related, use for the memory is to store authorization information for interested parties. Such information would be useful if the component failure notification system 10 were to function on a pull rather than push protocol. Therefore, in a situation where interested parties make requests to the routing device 40, the routing device 40 would compare the identity of the requesting parties to ensure that the parties have permission to receive an alert. It is also possible to control the sending of alerts in response to requests by the subject matter of the alert by comparing it to subject matter authorized parties can receive.

In all of the embodiments of the memory, the information relating interested parties to the alerts they can receive may be stored in a database. Alternatively, the memory may be organized such that any data structure relating the stored information may be used.

A further element of the component failure notification system is the alert. The alert may be a grouping of information formatted in a number of different ways, for example, in a text file or an XML file. Any alert to notify interested parties of a component failure must include at least the component which failed. Further information may be included in the alert, such as the specific failure of the component, vehicle identification information for the vehicle related to the failed vehicle component, diagnostic test information of the failed vehicle component, and symptom information related to the failed vehicle component. The alert may also contain environmental information and information such as where the alert originated. It may further be possible to customize the alerts such that only information desired by the recipient or the sender is included.

Figure 4:
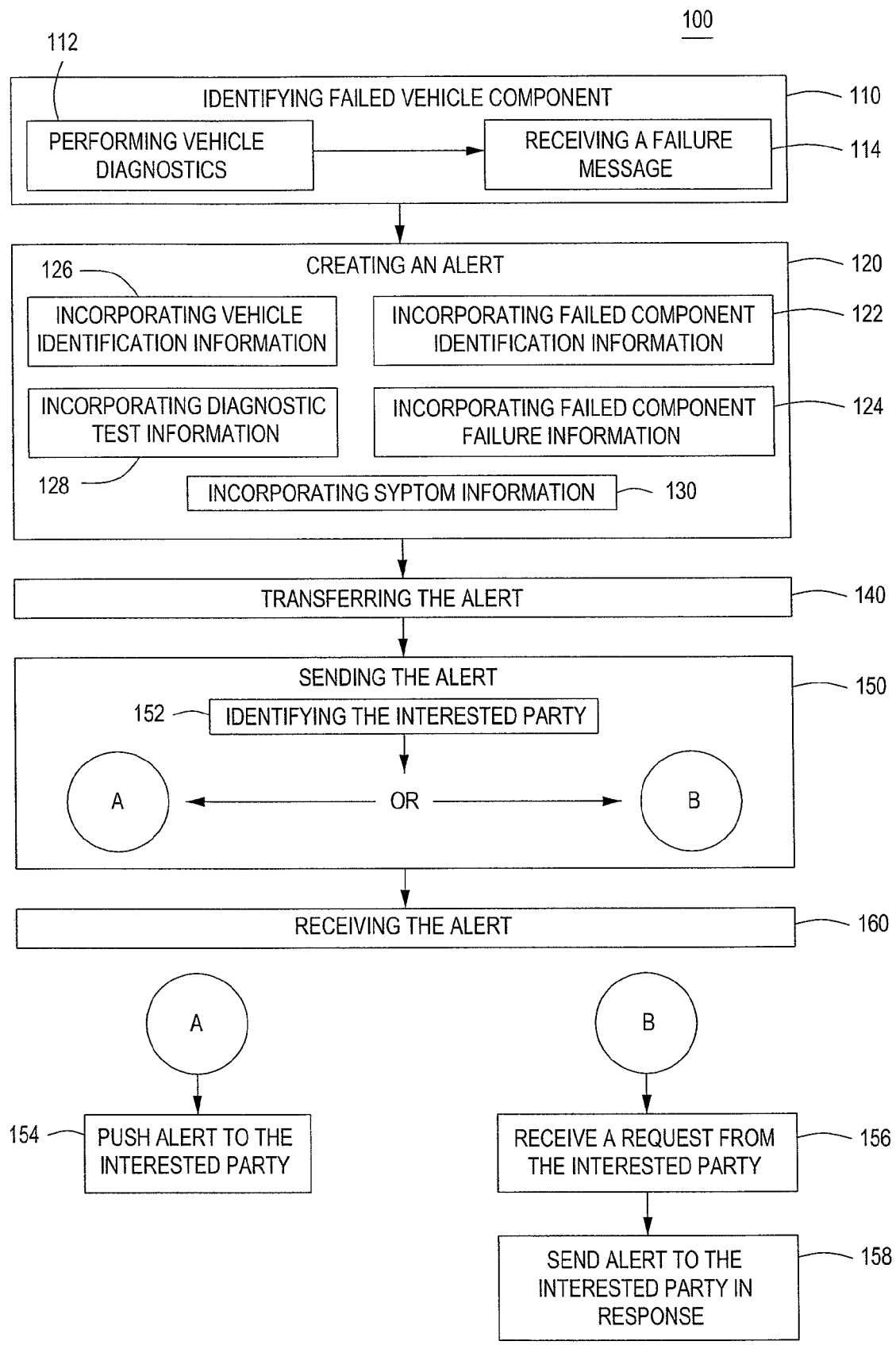
FIG. 4 is a flowchart illustrating steps that may be followed to notify interested parties upon component failure.

Referring now to FIG. 4, a flowchart diagram depicts an embodiment of the method for notifying interested parties 100. The method begins by identifying a failed vehicle component through analysis (step 110), such as might be done by a technician or a vehicle diagnostic tool. It may be that a technician uses a portable vehicle diagnostic tool to aid in making the diagnosis that a component has failed, and as to why it failed. Alternatively, certain vehicle diagnostic tools have the capability to diagnose failed components and the reasons why they failed for the technician. In either instance, identifying the vehicle component (step 110) may include performing vehicle diagnostic procedures using a portable vehicle diagnostic tool (step 112), and receiving a message indicating a failure and the failed vehicle component (step 114).

Once the determination has been made as to which component has failed, and potentially as to why it failed, the information is then used in creating an alert (step 120). The information that is to be a part of the alert may be entered into the component failure notification system manually by a user, or it may automatically transfer from the portable vehicle diagnostic tool to the reporting device. Once the information is in the component failure notification system, the reporting device may use the information to format it into an alert. The reporting device can incorporate any information that is available about the failed component. The reporting device should at least incorporate identity information (such as part name and number) for the failed vehicle component (step 122) and potentially the failure that occurred (step 124).

The reporting device may also incorporate vehicle identification information for a vehicle related to the failed vehicle component (step 126). Incorporating diagnostic test information related to the failed vehicle component (step 128) and incorporating symptom information related to the failed vehicle component (step 130) could also be executed by the reporting device. Any of the information to be incorporated into an alert may be customized by either the sender or the recipient. In this way, the information sent can be tailored to the needs of the parties using the system. Such customization may reduce the traffic on the system by only sending the desired information and not superfluous information.

After generating the alert, the alert is transferred to the routing device from the reporting device (step 140). Depending on the structure of the component failure notification system, i.e. whether or not the routing devices are separate or integrated with the other components, the alert is transferred either over the communications network 60 or the internal data link.

Once received by the routing device, the alert is sent to the interested parties (step 150). In sending the alert (step 150), the routing device must first identify the interested parties (step 152). One such method includes identifying the interested parties from a data structure, stored on a memory, containing information relating the interested parties with information that may exist in the alert. When the interested parties have been identified, the routing device may push the alert to the interested parties (step 154). Pushing the alert may be accomplished through different technologies, such as email and instant message.

Alternatively, the reporting device may receive a request for the alert from the interested parties (step 156). When a request for an alert is received, then the routing device may identify the interested parties (step 152) by identifying the interested parties from a data structure, stored on a memory, containing information associating the interested parties with the alert. Once the parties who have solicited a request for information have been identified, then the routing device may respond to the request by sending the alert from the routing device to the interested parties which sent the request (step 158). An example of this type of pull protocol that might be implemented is RSS.

Finally, it may be part of the method to receive the alert (step 160) on a receiving device belonging to interested parties.

FIGS. 1, 2, 3, and 4 are schematic diagrams and flowcharts of methods and systems according to various embodiments of the present invention. It will be understood that each step of the flowchart illustration, and combinations of steps in the flowchart illustration, can be implemented by computer program instructions or other means. Although computer program instructions are discussed, an apparatus according to the present invention can include other means, such as hardware or some combination of hardware and software, including one or more processors or controllers, for performing the disclosed functions.

In this regard, FIGS. 1, 2, and 3 depict the system of various embodiments potentially including a general-purpose computer by which the embodiments of the present invention may be implemented. Those of ordinary skill in the art will appreciate that a computer can include many more components than those described herein. However, it is not necessary that all of these generally conventional components be shown in order to disclose an illustrative embodiment for practicing the invention. The general-purpose computer can include a processing unit, and a system memory, which may include random access memory (RAM) and read-only memory (ROM). The computer also may include nonvolatile storage memory, such as a hard disk drive, where additional data can be stored.

An embodiment of the present invention can also include one or more input devices, such as a mouse, keyboard, and the like. A display can be provided for viewing text and graphical data, as well as a user interface to allow a user to request specific operations. Furthermore, an embodiment of the present invention may be connected to one or more remote computers via a communication device. The connection may be over a communication network 60, such as a local area network (LAN) wide area network (WAN), and can include all of the necessary circuitry for such a connection.

Typically, computer program instructions, such as portions of the method for notifying interested parties 100, may be loaded onto the computer or other general purpose programmable machine to produce a specialized machine, such that the instructions that execute on the computer or other programmable machine create means for implementing the functions specified in the flowchart. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the flowchart.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the flowchart steps.

Accordingly, steps of the flowchart support combinations of means for performing the specified functions, combinations of steps for performing the specified functions and program instruction means for performing the specified functions. It will also be understood that each step of the flowchart, as well as combinations of steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for notifying an interested party of a component failure, comprising the steps of:
   performing vehicle diagnostic procedures using a portable vehicle diagnostic tool;
   identifying a failed vehicle component through vehicle diagnostics with the portable vehicle diagnostic tool;
   creating an alert, in a reporting device of the portable vehicle diagnostic tool, by incorporating identity information and failure information for the failed vehicle component;
   transferring the alert to a routing device of the portable vehicle diagnostic tool; and
   sending the alert from the routing device of the portable vehicle diagnostic tool via electronic communication to the interested party.

2. The method of claim 1, wherein creating the alert further includes the step of incorporating vehicle identification information for a vehicle related to the failed vehicle component.

3. The method of claim 1, wherein creating the alert further includes the step of incorporating diagnostic test information related to the failed vehicle component.

4. The method of claim 1, wherein creating the alert further includes the step of incorporating symptom information related to the failed vehicle component.

5. The method of claim 1, wherein identifying the failed vehicle component further includes the step of:
   receiving a message indicating a failure and the failed vehicle component.

6. The method of claim 5, wherein creating the alert further includes the step of manually entering the identity information and the failure information into a reporting device, wherein the identity information includes at least the failed vehicle component, and the failure information includes at least the failure.

7. The method of claim 5, wherein creating the alert further includes the step of automatically entering the identity information and the failure information into a reporting device, wherein the identity information includes at least the failed vehicle component, and the failure information includes at least the failure.

8. The method of claim 1, wherein sending the alert further includes the step of identifying the interested party from a data structure stored on a memory, wherein the data structure contains information associating the interested party with the alert.

9. The method of claim 8, wherein sending the alert further includes the steps of receiving a request for the alert from the interested party to the routing device; and
   responding to the request by sending the alert from the routing device to the interested party which sent the request.

10. The method of claim 1, wherein sending the alert further includes the step of pushing the alert to the interested party.

11. The method of claim 1, further comprising the step of receiving the alert from the routing device on a receiving device.

12. A system for notifying an interested party, comprising:
   a portable vehicle diagnostic tool to identify a failed vehicle component and a related failure for the failed vehicle component;
   a reporting device communicatively connected to and integrated in the portable vehicle diagnostic tool, to create an alert containing information about the failed vehicle component and the failure identified by the portable vehicle diagnostic tool and to send the alert;
   a routing device communicatively connected to the reporting device and integrated in the portable vehicle diagnostic tool, to route the alert to the interested party;
   a memory communicatively connected to the routing device to store information relating the interested party with information that may exist in the alert; and
   a communication network communicatively connecting the portable vehicle diagnostic tool, the reporting device, and the routing device.

13. The system of claim 12, wherein the reporting device and the routing device are one unit.

14. The system of claim 12, wherein the portable vehicle diagnostic tool, the reporting device, and the routing device are one unit.

15. The system of claim 12, further comprising a receiving device communicatively connected to the routing device via the communication network.

16. The system of claim 12, further comprising a server communicatively connected to the reporting device via the communication network.

17. The system of claim 16, further comprising a receiving device communicatively connected to the routing device via the communication network.

18. The system of claim 12, wherein the information stored in the memory includes at least identification for the interested party and the interested party's interests.

19. The system of claim 12, wherein the alert further comprises vehicle identification information for a vehicle related to the failed vehicle component.

20. The system of claim 12, wherein the alert further comprises diagnostic test information related to the failed vehicle component.

21. The system of claim 12, wherein the alert further comprises symptom information related to the failed vehicle component.

22. A system for notifying an interested party, comprising:
   means for identifying a failed vehicle component;
   means for creating an alert by incorporating identity information and failure information for the failed vehicle component;
   means for sending the alert via electronic communication to the interested party;
   means for transferring the alert to the means for sending; and
   a means for communicatively connecting the means for identifying, the means for creating, means for sending, and the means for transferring; and
   a means for integrating the means for communicatively connecting, the means for identifying, the means for creating, means for sending, and the means for transferring.

* * * * *